(12) United States Patent
Rosenberg et al.

(10) Patent No.: US 9,018,401 B2
(45) Date of Patent: Apr. 28, 2015

(54) PROCESS FOR PRODUCING (ETHYNE-1,2-DIYL(BIS(ISOBENZOFURAN-1,3-DIONE)

(71) Applicant: Nexam Chemical AB, Lund (SE)

(72) Inventors: Jan-Erik Rosenberg, Falkenberg (SE); Daniel Rome, Lund (SE); Erik Lager, Lund (SE); Dane Momcilovic, Lund (SE)

(73) Assignee: Nexam Chemical AB, Lund (SE)

( * ) Notice: Subject to any disclaimer, the term of this patent is extended or adjusted under 35 U.S.C. 154(b) by 0 days.

(21) Appl. No.: 14/394,489

(22) PCT Filed: Mar. 8, 2013

(86) PCT No.: PCT/EP2013/054686
§ 371 (c)(1),
(2) Date: Oct. 15, 2014

(87) PCT Pub. No.: WO2013/156200
PCT Pub. Date: Oct. 24, 2013

(65) Prior Publication Data
US 2015/0080586 A1    Mar. 19, 2015

(30) Foreign Application Priority Data
Apr. 20, 2012 (EP) .................... 12164900

(51) Int. Cl.
*C07D 307/89* (2006.01)
*C07C 51/567* (2006.01)

(52) U.S. Cl.
CPC .................... *C07D 307/89* (2013.01)

(58) Field of Classification Search
CPC .................... C07D 307/89; C07C 51/567
See application file for complete search history.

(56) References Cited

U.S. PATENT DOCUMENTS

| | | |
|---|---|---|
| 3,956,322 A | 5/1976 | Quinn et al. |
| 3,983,093 A | 9/1976 | Williams, III et al. |
| 4,973,707 A | 11/1990 | Nye |
| 5,185,454 A | 2/1993 | Bader et al. |
| 5,567,800 A | 10/1996 | Hergenrother et al. |
| 2005/0215820 A1 | 9/2005 | Urazoe et al. |

FOREIGN PATENT DOCUMENTS

| | | |
|---|---|---|
| WO | 2011/128431 A1 | 10/2011 |
| WO | 2012/131063 A1 | 10/2012 |

OTHER PUBLICATIONS

International Search Report for corresponding International Application No. PCT/EP2013/054686 dated May 6, 2013.
Walsh et al., "A New Class of Aromatic Dianhydrides for Thermostable Polyimides", Chem. Mater, vol. 13, 2001, pp. 2472-2475.

*Primary Examiner* — Sun Jae Yoo
(74) *Attorney, Agent, or Firm* — Renner, Otto, Boisselle & Sklar, LLP

(57) ABSTRACT

A process for obtaining (ethyne-1,2-diyl)bis(isobenzofuran-1,3-dione) is disclosed. In the disclosed process chloro-, bromo-, or iodoisobenzofuran-1,3-dione is reacted with ethyne in a solvent in the presence of a dissolved homogenous palladium catalyst, optionally a copper salt, a base, and optionally a solvent distinct from said base. Subsequently the obtained (ethyne-1,2-diyl)bis(isobenzofuran-1,3-dione) may be washed with a washing agent, such as a carboxylic acid, a polar aprotic solvent, or chloroform.

21 Claims, No Drawings

PROCESS FOR PRODUCING (ETHYNE-1,2-DIYL(BIS(ISOBENZOFURAN-1,3-DIONE)

This application is a national phase of International Application No. PCT/EP2013/054686 filed Mar. 8, 2013 and published in the English language, which claims priority to Application No. EP 12164900.8 filed Apr. 20, 2012.

FIELD OF THE INVENTION

The present invention relates to a process for producing a (ethyne-1,2-diyl)bis(isobenzofuran-1,3-dione), such as 5,5'-(ethyne-1,2-diyl)bis(isobenzofuran-1,3-dione), in high yield and in high purity, preferably with low halogen content.

BACKGROUND

Aromatic polyimides represent a class of high-end polymers. They have inherent good properties, such as wear and friction properties, good electrical properties, radiation resistance, good cryogenic temperature stability and good flame retardant properties. Therefore, aromatic polyimides are used in the electronics industry for flexible cables, as an insulating film on magnet wire and for medical tubing. Polyimide materials are also used in high or low temperature exposed applications as structural parts where the good temperature properties are a prerequisite for the function.

Various types of aromatic carboxylic acid dianhydride monomers and aromatic diamine monomers have been used to obtain various types of aromatic polyimides. Examples of aromatic carboxylic acid dianhydride monomers which have been used include pyromellitic dianhydride, 4,4'-oxydiphthalic anhydride, 2,2-bis-[4-(3,4-dicarboxyphenoxyl)phenyl]-propane dianhydride, 3,3',4,4'-benzophenonetetracarboxylic acid dianhydride or 3,3',4,4'-tetracarboxybiphenyl dianhydride. Examples of aromatic diamine monomers which have been used include 4,4'-oxydianiline, 1,4-diaminobenzene, 1,3-diaminobenzene, 1,3-bis-(4-aminophenoxyl)benzene, 1,3-bis-(3-aminophenoxyl)benzene, methylenedianiline or 3,4'-oxydianiline.

Williams and Donahue, (U.S. Pat. No. 3,983,093) have shown that the solvent resistance of polyeytherimides may be improved by using a rigid aromatic carboxylic acid dianhydride, such as pyromellitic dianhydride or 3,3',4,4'-benzophenonetetracarboxylic acid dianhydride, in addition to an aromatic carboxylic acid ether dianhydride, such as 2,2-bis-[4-(3,4-dicarboxyphenoxyl)phenyl]-propane dianhydride. Further, a related rigid aromatic carboxylic acid dianhydride, i.e. 5,5'-((ethyne-1,2-diylbis(4,1-phenylene))bis(oxy))bis(isobenzofuran-1,3-dione), is described in U.S. Pat. No. 3,956,322.

Furthermore, U.S. Pat. No. 4,973,707 relates to the discovery that polyacetyleneimides, resulting from the intercondensation of an acetylene-di(phthalic anhydride) and an aryl diamine, have high glass transition temperatures, excellent solvent resistance, and improved rigidity compared to polyacetyleneimides of the prior art. The same properties in other polyimides may, according to U.S. Pat. No. 4,973,707, be enhanced by the presence of units derived from 1,2-acetylene di(phthalic anhydride).

According to U.S. Pat. No. 4,973,707, 5,5'-(ethyne-1,2-diyl)bis(isobenzofuran-1,3-dione) may be synthesized in several steps from ethynyltrimethylsilane and 5-bromo-2-methylisoindoline-1,3-dione. In the described synthesis, 5,5'-(ethyne-1,2-diyl)bis(2-methylisoindoline-1,3-dione) is hydrolyzed and subsequently dehydrated to obtain 5,5'-(ethyne-1,2-diyl)bis(isobenzofuran-1,3-dione). Alternatively, 5,5'-(ethyne-1,2-diyl)bis(2-methylisoindoline-1,3-dione) may be obtained in moderate yield by coupling of 2 equivalents of 5-bromo-2-methylisoindoline-1,3-dione with 1 equivalent acetylene. The two proposed synthetic routes provide 5,5'-(ethyne-1,2-diyl)bis(isobenzofuran-1,3-dione) only in low yields (10% and 23%, respectively). Thus, neither of the two proposed routes provide 5,5'-(ethyne-1,2-diyl)bis(isobenzofuran-1,3-dione) in a yield acceptable for industrial scale.

In Chemistry of Materials, 2001, 13, 2472-2475, a three step procedure for obtaining 4,4'-(ethyne-1,2-diyl)bis(isobenzofuran-1,3-dione) from diethyl 3-iodophthalate in moderate yield (52%) is disclosed.

In addition to the use of rigid aromatic carboxylic acid dianhydride, other ways for improving various properties, such as mechanical properties, of polyimides for use in airplanes and aerospace applications are known in the art.

As an example, the processability of polyimides may be improved by introducing cross-linking monomers into the polymer. As the resulting polymer chains may be cross-linked, they may be shorter whilst the mechanical properties are maintained or even improved. Shorter polymer chains have the advantage of being easier to process, as the viscosity of the polymer melt is lower. Examples of such cross-linking technologies include bismaleimides and nadimide-based PMR resins, which undergo cure at temperatures near 250° C. However, such thermoset polyimides will not withstand oxidative degradation on long-term exposure at temperatures above 200° C., as the cross-linking moieties have inferior thermal stability, compared to the oligoimide units.

In attempts to improve the thermal stability, thermoset polyimides containing phenylethynyl-substituted aromatic species as the reactive end-cappers have been developed. U.S. Pat. No. 5,567,800 discloses phenylethynyl terminated imide oligomers (PETIs). Such oligomers may be prepared by firstly preparing amino terminated amic acid oligomers from dianhydride(s) and a slight excess of diamine(s) and subsequently end-cap the resulting amino terminated amic acid oligomers with phenylethynyl phtalic anhydride (PEPA). The amic acid oligomers are subsequently dehydrated to the corresponding imide oligomers. Upon heating the triple bonds will react and cross-link the end-capped polyimid, thereby improving its heat resistance and mechanical strength.

A process for producing aryl ethynyl phthalic acid, e.g. phenylethynyl phtalic anhydride (PEPA), and derivatives thereof (including fluorine-containing compounds), in which an aryl ethynyl phthalic anhydride is formed by subjecting an aryl phthalic acid to ring closing is disclosed in US 2005/215820.

However, in some applications there is a need for further improving the heat resistance and mechanical strength of PETI. Especially, it would be of interest to allow for improving the mechanical strength of PETI further. In curing of ethynyl group modified oligomers and polymers, such as PETI, the curing temperature and yield of cross-linking is to a large extent determined by the mobility of the ethynyl group. A more mobile group will have a lower curing temperature and give rise to higher yield of cross-linking. Hence, ethynyl groups used in the art for cross-linking has typically been positioned at the ends of the oligomers and polymers to be cross-linked, cf. PETI, as the end-groups will have higher mobility compared to other parts of the oligomers and polymers.

The degree of cross-linking, which may be achieved, is inherently linked to the ratio of cross-linking groups and polymer chains. The portion of cross-linking end groups may be increased by decreasing the length of the polymer chains.

However, decreasing the length of the polymer chains will lower the heat resistance and especially the mechanical strength. Further, the polymeric properties will be decreased and eventually lost if the length of the polymer chains is decreased.

The present inventors have found (cf. WO 2012/131063), that the degree of cross-linking may be enhanced by combining the use of an phenylethynyl terminated end-capper, such as PEPA (cf. U.S. Pat. No. 5,567,800) or PETA (cf. WO 2011/128431), with use of an acetylene-di(phthalic anhydride), such as 5,5'-(ethyne-1,2-diyl)bis(isobenzofuran-1,3-dione).

However, in order for such a combined concept to find wide spread industrial application, there is need for an alternative synthetic route to provide 5,5'-(ethyne-1,2-diyl)bis(isobenzofuran-1,3-dione) and related (ethyne-1,2-diyl)bis(isobenzofuran-1,3-diones) in high yields and adequate purity. Especially, the obtained 5,5'-(ethyne-1,2-diyl)bis(isobenzofuran-1,3-dione) should preferably have low halogen content, as halogens catalyze degradation of polyimides at high temperatures. Further, halogen may hamper the incorporation of 5,5'-(ethyne-1,2-diyl)bis(isobenzofuran-1,3-dione) into polyimides as the imidization is negatively affected by the presence of halogens. In addition, the isolating effect, being an essential property of polyimide films used in electronics, is negatively affected by the presence of halogens and the risk for treeing is thereby increased.

According to U.S. Pat. No. 5,185,454, the halogen content of di-aryl acetylenes obtained via Sonagashira couplings may be reduced via treatment with water. While 5,5'-(ethyne-1,2-diyl)bis(2-methylisoindoline-1,3-dione) may be washed with water to reduce the halogen content, 5,5'-(ethyne-1,2-diyl)bis(isobenzofuran-1,3-dione) may not, without hydrolyzing the carboxylic moiety, be washed with water.

Thus, there is need within the art for a process for obtaining 5,5'-(ethyne-1,2-diyl)bis(isobenzofuran-1,3-dione) in high yields and adequate purity for incorporation into polyimides.

SUMMARY

Accordingly, the present invention preferably seeks to mitigate, alleviate, eliminate or circumvent one or more of the above-identified deficiencies in the art and disadvantages singly or in any combination and solves at least the above mentioned problems by providing a process for obtaining (ethyne-1,2-diyl)bis(isobenzofuran-1,3-dione) comprising the steps of:
  reacting a chloro-, bromo-, or iodoisobenzofuran-1,3-dione with ethyne in an aprotic solvent, and in the presence of a dissolved, homogenous palladium catalyst, a base, and optionally a solvent distinct from the base, to obtain precipitated (ethyne-1,2-diyl)bis(isobenzofuran-1,3-dione);
  separating the obtained precipitated (ethyne-1,2-diyl)bis(isobenzofuran-1,3-dione) from the reaction mixture.

According to an aspect of the invention, the process comprises the step of washing the precipitated (ethyne-1,2-diyl)bis(isobenzofuran-1,3-dione) with a washing agent distinct from water and which dissolves the formed chloro, bromo or iodo salt of said base. Such washing agent may be selected from the group consisting of carboxylic acids, such as formic acid or acetic acid, polar aprotic solvents, such as dimethylformamide, dimethylacetamide, dimethylsulfoxide, and N-Methyl-2-pyrrolidone, and chloroform. The washing agent may be a C1-5 alkanoic acid, such as formic acid or acetic acid.

According to an aspect of the invention, a 5-haloisobenzofuran-1,3-dione, such as 5-bromoisobenzofuran-1,3-dione, is reacted with ethyne to obtain 5,5'-(ethyne-1,2-diyl)bis (isobenzofuran-1,3-dione).

According to an aspect of the invention, the reaction between the chloro-, bromo- or iodoisobenzofuran-1,3-dione and ethyne is performed in the presence of a copper salt, such as copper (I) chloride, bromide, or iodide, or copper (I) acetate.

According to an aspect of the invention, the precipitated (ethyne-1,2-diyl)bis(isobenzofuran-1,3-dione) is washed with a carboxylic acid, e.g. acetic acid, followed by a polar aprotic solvent, such as dimethylformamide, dimethylacetamide, dimethylsulfoxide, or N-Methyl-2-pyrrolidone.

Further advantageous features of the invention are defined in the dependent claims and described in embodiments disclosed herein

DESCRIPTION OF EMBODIMENTS

Definitions

In the context of the present application and invention, the following definitions apply:

As used herein, "alkyl" used alone or as a suffix or prefix, is intended to include both branched and straight chain saturated aliphatic hydrocarbon groups having from 1 to 12 carbon atoms, or if a specified number of carbon atoms is provided then that specific number is intended. For example "C1-6 alkyl" denotes alkyl having 1, 2, 3, 4, 5 or 6 carbon atoms. When the specific number denoting the alkyl-group is the integer 0 (zero), a hydrogen-atom is intended as the substituent at the position of the alkyl-group. For example, "N(C0 alkyl)$_2$" is equivalent to "NH2" (amino).

As used herein, "alkylenyl" or "alkylene" used alone or as a suffix or prefix, is intended to include straight chain saturated aliphatic hydrocarbon groups having from 1 to 12 carbon atoms or if a specified number of carbon atoms is provided then that specific number is intended. For example "C1-6 alkylenyl" "C1-6 alkylene" denotes alkylenyl or alkylene having 1, 2, 3, 4, 5 or 6 carbon atoms. When the specific number denoting the alkylenyl or alkylene-group is the integer 0 (zero), a bond is intended to link the groups onto which the alkylenyl or alkylene-group is substituted. For example, "NH(C0 alkylene)NH$_2$" is equivalent to "NHNH$_2$" (hydrazino). As used herein, the groups linked by an alkylene or alkylenyl-group are intended to be attached to the first and to the last carbon of the alkylene or alkylenyl-group. In the case of methylene, the first and the last carbon is the same. For example, "H$_2$N(C2 alkylene)NH$_2$", "H$_2$N(C3 alkylene) NH$_2$", "N(C4 alkylene)", "N(C5 alkylene)" and "N(C2 alkylene)$_2$NH" is equivalent to 1,2-diamino ethane, 1,3-diamino propane, pyrrolidinyl, piperidinyl and piperazinyl, respectively.

Examples of alkyl include, but are not limited to, methyl, ethyl, n-propyl, i-propyl, n-butyl, i-butyl, sec-butyl, t-butyl, pentyl, and hexyl.

Examples of alkylene or alkylenyl include, but are not limited to, methylene, ethylene, propylene, and butylene.

As used herein, alkoxy is intended to mean an —O-alkyl group. Examples of alkoxy, includes methoxy, i.e. —O-Me, ethoxy, i.e. —O-Et, and iso-propoxy —OCH(CH$_3$)$_2$ As used herein, the term "aryl" refers to a ring structure, comprising at least one aromatic ring, made up of from 5 to 14 carbon atoms. Ring structures containing 5, 6, or 7 carbon atoms would be single-ring aromatic groups, for example phenyl. Ring structures containing more than 7 carbon atoms, such as 8, 9, 10, 11, 12, 13, or 14 carbon atoms would be polycyclic, for example naphthyl. The aromatic ring may be substituted at one or more ring positions. The term "aryl" also includes polycyclic ring systems having two or more cyclic rings in which two or more carbons are common to two adjoining rings (the rings are "fused rings") wherein at least one of the rings is aromatic, for example, the other cyclic rings may be cycloalkyls, cycloalkenyls, cycloalkynyls, aryls and/ or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

As used herein, "heteroaryl" refers to an aromatic heterocycle, having at least one ring with aromatic character, (e.g. 6 delocalized electrons) or at least two conjugated rings with aromatic character, (e.g. 4n+2 delocalized electrons where "n" is an integer), and comprising up to about 14 carbon atoms, and having at least one heteroatom ring member such as sulfur, oxygen, or nitrogen. Heteroaryl groups include monocyclic and bicyclic (e.g. having 2 fused rings) systems.

Examples of heteroaryl groups include without limitation, pyridyl (i.e., pyridinyl), pyrimidinyl, pyrazinyl, pyridazinyl, triazinyl, furyl (i.e. furanyl), quinolyl, tetrahydroquinolyl, isoquinolyl, tetrahydroisoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, benzimidazolyl, indolinyl, and the like.

Embodiments

The present inventors have found that (ethyne-1,2-diyl)bis (isobenzofuran-1,3-diones), such as 5,5'-(ethyne-1,2-diyl)bis (isobenzofuran-1,3-dione), may be obtained in a high yield in a one-step procedure by employing a Sonogashira coupling to react a chloro-, bromo-, or iodoisobenzofuran-1,3-dione, such as 5-chloro-, 5-bromo-, or 5-iodoisobenzofuran-1,3-dione, with acetylene, i.e. ethyne. By employing a one step procedure and by avoiding aqueous work-up, causing hydrolysis of the anhydride moieties, a (ethyne-1,2-diyl)bis (isobenzofuran-1,3-dione), such as 5,5'-(ethyne-1,2-diyl)bis (isobenzofuran-1,3-dione), may be obtained in significantly higher yield and shorter process time compared to known processes.

Further, by choosing reaction conditions in a manner such that the formed (ethyne-1,2-diyl)bis(isobenzofuran-1,3-dione) precipitates, (ethyne-1,2-diyl)bis(isobenzofuran-1,3-dione) may easily be separated from reaction mixture; especially if a dissolved, homogenous palladium catalyst is used.

The purity of the thus obtained (ethyne-1,2-diyl)bis (isobenzofuran-1,3-dione) may be increased by washing it with a washing agent dissolving the chloro, bromo or iodo salt of said base being formed during the reaction. The washing agent should be selected from washing agents not reacting with the anhydride moiety to any extent. Thus, water is not a washing agent in the present context. Similarly, the washing agent should preferably not be selected among alcohols, such as methanol and ethanol, ammonia, and primary and secondary amines, all being nucleophilic, i.e. being able to cause solvolysis of the anhydride moiety.

According to an embodiment, the washing agent to be employed have low water content, e.g. less than 0.1 wt %, such as less than 100 ppm by weight, or is even essentially anhydrous.

Examples of preferred washing agents encompass carboxylic acids, such as formic acid or acetic acid, polar aprotic solvents, such as dimethylformamide, dimethylacetamide, dimethylsulfoxide, and N-Methyl-2-pyrrolidone, and chloroform.

By using such a one step procedure and optionally including a washing step, a (ethyne-1,2-diyl)bis(isobenzofuran-1, 3-dione), such as 5,5'-(ethyne-1,2-diyl)bis(isobenzofuran-1, 3-dione), may be obtained in high purity and high yield.

Accordingly, an embodiment relates to a process for obtaining a (ethyne-1,2-diyl)bis(isobenzofuran-1,3-dione), such as 5,5'-(ethyne-1,2-diyl)bis(isobenzofuran-1,3-dione). The process comprises the step of reacting a chloro-, bromo-, or iodoisobenzofuran-1,3-dione, preferably a 5-chloro-, 5-bromo-, or 5-iodoisobenzofuran-1,3-dione, such as 5-bromoisobenzofuran-1,3-dione, with ethyne in a solvent. The coupling is performed in the presence of a dissolved homogenous palladium catalyst and optionally a copper salt. As a homogenous palladium catalyst, dissolved in the solvent, is employed, the formed (ethyne-1,2-diyl)bis(isobenzofuran-1, 3-dione), precipitating from the reaction mixture, may be filtered off, and thus separated from the dissolved homogenous palladium catalyst. Accordingly, the use of a dissolved homogenous palladium catalyst and reaction conditions causing the (ethyne-1,2-diyl)bis(isobenzofuran-1,3-dione) to precipitate once formed, will imply that that the work-up of the reaction mixture may be performed without affecting the yield of the (ethyne-1,2-diyl)bis(isobenzofuran-1,3-dione) to any large extent.

The reaction is performed in the presence of a base as well. Once the chloro-, bromo-, or iodoisobenzofuran-1,3-dione is coupled with ethyne, the base will become protonated and typically form a chloride, bromide, or iodide salt. As the anhydride moieties of the starting material and the product are labile and may be opened by nucleophiles, the base should preferably be aprotic. Similarly, the base should not be a nucleophilic base, such as an alcolate, e.g. sodium ethoxide, lithium amide, potassium amide or calcium amide. Although the base may be liquid and thereby acting as solvent as well, the reaction will typically be performed in a solvent distinct from the base.

Preferably, the reaction is performed at elevated temperature. The elevated temperature may correspond to the boiling point of the base, if liquid and used as solvent, or to the boiling point of a solvent distinct from the base, i.e. at reflux of the solvent. According to an embodiment, the reaction is performed at a temperature of 50 to 150° C., such as at a temperature 60 to 100° C.

The reaction is typically performed under ethyne atmosphere, with stirring of the reaction mixture. Preferably, an overpressure of ethyne is employed. Alternatively, but less preferred for industrial scale processes, ethyne may be added to the reaction mixture by purging the reaction mixture with ethyne, at atmospheric pressure.

Once the (ethyne-1,2-diyl)bis(isobenzofuran-1,3-dione) has been formed and precipitated, it is separated from the reaction mixture; typically by filtration.

As described, the base will typically become protonated and form a chloride, bromide, or iodide salt during the coupling reaction. The formed salt may contaminate the precipitated (ethyne-1,2-diyl)bis(isobenzofuran-1,3-dione). Thus, the precipitated (ethyne-1,2-diyl)bis(isobenzofuran-1,3-dione) may be washed with a washing agent dissolving the formed chloro, bromo or iodo salt. Such a wash may be performed before and/or after the separation of the obtained precipitated (ethyne-1,2-diyl)bis(isobenzofuran-1,3-dione) from the reaction mixture. If the wash is to be performed before the separation of the precipitated (ethyne-1,2-diyl)bis (isobenzofuran-1,3-dione), the washing agent may simply be added to the reaction mixture before separating the precipitated (ethyne-1,2-diyl)bis(isobenzofuran-1,3-dione). In such an embodiment, the washing agent is typically added once the reaction is completed. Further, the precipitated (ethyne-1,2-diyl)bis(isobenzofuran-1,3-dione) is typically further washed after having been separated from the reaction mixture.

If the reaction between the chloro-, bromo-, or iodoisobenzofuran-1,3-dione and ethyne is performed in a solvent dissolving the formed chloro, bromo or iodo salt, or if a high halogen content is acceptable for the intended use of the product, the need to wash the precipitated (ethyne-1,2-diyl)bis(isobenzofuran-1,3-dione) may be dispensed with. However, also in embodiments, wherein solvents dissolving the formed chloro, bromo or iodo salt, such as polar aprotic solvents, are being used as solvent for the reaction between the chloro-, bromo-, or iodoisobenzofuran-1,3-dione and ethyne, it may be advantageous to employ a washing step in order to reduce the halogen content in the precipitated (ethyne-1,2-diyl)bis(isobenzofuran-1,3-dione).

As an example, the precipitated (ethyne-1,2-diyl)bis(isobenzofuran-1,3-dione) may subsequently be washed with a carboxylic acid. It was found that washing the precipitated (ethyne-1,2-diyl)bis(isobenzofuran-1,3-dione) with a carboxylic acid is an efficient way of removing the chloride, bromide, or iodide salt, such as triethylammonium bromide, formed during the reaction without affecting the yield of (ethyne-1,2-diyl)bis(isobenzofuran-1,3-dione) significantly.

Evidently, the separated (ethyne-1,2-diyl)bis(isobenzofuran-1,3-dione) may be washed with more than one aliquot of a washing agent, such as a carboxylic acid.

The wash may be performed by dispersing the precipitated (ethyne-1,2-diyl)bis(isobenzofuran-1,3-dione), before or after having been separated from the reaction mixture, in the washing agent, e.g. a carboxylic acid, and heating and stirring the resulting slurry. The slurry may be heated to between 25 and 125° C., such as 40 and 75° C. Subsequently to the stirring, the (ethyne-1,2-diyl)bis(isobenzofuran-1,3-dione) may be filtered of. The slurry may be stirred for 1 hour to 24 hours, such as for 1 to 4 hours.

As already mentioned, the washing agent may be a carboxylic acid. Preferably the carboxylic acid is an unsubstituted C1-5 alkanoic acid, i.e. C1-4 alkyl-COOH or HCOOH, such as formic acid or acetic acid. However, also substituted C1-5 alkanoic acids, such as trifluoroacectic acid or chloroacetic acid, may be used, but unsubstituted C1-5 alkanoic acids are preferred. According to an embodiment, the carboxylic acid employed in the process described herein is glacial, i.e. anhydrous, acetic acid. In order to avoid hydrolysis of the anhydride, the employed carboxylic acid should preferably be anhydrous. Also other types of washing agents to be employed should preferably be anhydrous.

Further examples of washing agents include polar aprotic solvents, such as dimethylformamide, dimethylacetamide, dimethylsulfoxide, and N-Methyl-2-pyrrolidone, and chloroform. While also polar aprotic solvents dissolve the salt fairly effective, although not as effective as carboxylic acids, they also to some very limited extent dissolve the (ethyne-1,2-diyl)bis(isobenzofuran-1,3-dione) as well, thus effecting the yield to some extent. Accordingly, the preferred washing agent, as outlined above, is a carboxylic acid.

According to an embodiment, aprotic, in polar aprotic solvent, as used herein, refers to solvents not having a hydrogen atom bound to an oxygen or nitrogen atom, thereby not being able to donate a hydrogen atom. Further, polar, in polar aprotic solvent refers to solvents having a dielectric constant of at least 6.0, preferably at least 20, or a dipole moment of at least 1.5 debye, preferably at least 2.5 debye.

Similarly, according to an embodiment, aprotic, in aprotic base, as used herein, refers to bases not having a hydrogen atom bound to an oxygen or nitrogen atom in its neutral form, thereby not being able to lose a hydrogen atom subsequently to having acted as nucelophiles. Pyridine and triethylamine are two examples of an aprotic base, While a wash with a carboxylic acid is sufficient to obtain (ethyne-1,2-diyl)bis(isobenzofuran-1,3-dione) with high purity, the halogen content may anyhow be too high for some applications, such as the use of (ethyne-1,2-diyl)bis(isobenzofuran-1,3-dione) as cross-linker in polyimides for electronics. In order to decrease the halogen content, e.g. the bromide content, even further, the (ethyne-1,2-diyl)bis(isobenzofuran-1,3-dione) may be washed with a polar aprotic solvent, such as dimethyl acetamide or dimethylformamide.

Although, carboxylic acids are effective in dissolving the formed chloride, bromide, or iodide salt, some chloride, bromide, or iodide salt are entrapped in the precipitated (ethyne-1,2-diyl)bis(isobenzofuran-1,3-dione). It was found, that a second wash with a polar aprotic solvent is an effective way of dissolving such entrapped salt. Less quantity of polar aprotic solvent can to be used if applied in a second washing step, subsequent to a washing step with a carboxylic acid, compared to if applying a polar aprotic solvent as washing agent in the first wash. As less polar aprotic solvent is used, a higher yield of (ethyne-1,2-diyl)bis(isobenzofuran-1,3-dione) may be obtained.

Typically, separated, acid washed, solid (ethyne-1,2-diyl)bis(isobenzofuran-1,3-dione) is re-slurried in hot, e.g. 100 to 150° C., dimethylformamide and subsequently filtered off.

In order to provide dry (ethyne-1,2-diyl)bis(isobenzofuran-1,3-dione), the compound may be dried as a last step of the described process. As an example the compound may be dried under reduced pressure, such as less than 100 mbar, at elevated temperature, such as 50° C. to 150° C. According to one embodiment, the compound is dried under reduced pressure at elevated temperature, such as at a temperature of 75 to 125° C.

In order to facilitate the work up of the reaction mixture, and the purification of the formed (ethyne-1,2-diyl)bis(isobenzofuran-1,3-dione), a dissolved homogenous palladium catalyst is used in the reaction. Various examples of homogenous palladium catalyst are known within the art.

Examples of homogenous palladium catalysts comprise:
  complexed inorganic and organic palladium salts, wherein the complexing agents may be a nitrile, such as benzonitrile, or a C1-C4 alkyl nitril, such as acetonitrile, triphenylarsine, a phosphine according to formula (II) below, or a chelating diphosphine, such as BINAP (2,2'-bis(diphenylphosphino)-1,1'-binaphthyl), SEGPHOS (5,5'-Bis(diphenylphosphino)-4,4'-bi-1,3-benzodioxole), Xantphos (4,5-Bis(diphenylphosphino)-9,9-dimethylxanthene), 1,1'-Bis(diphenylphosphino)ferrocene (dppf), SPANphos (4,4,4',4',6,6'-Hexamethyl-2,2'-spirobichromane-8,8'-diylbis(diphenylphosphane)), dppm (1,1-Bis(diphenylphosphino)methane), dmpe (1,2-Bis(dimethylphosphino)ethane), dippe (1,2-Bis(diisopropylphosphino)ethane), dppe (1,2-Bis(diphenylphosphino)ethane), DIPAMP (Ethane-1,2-diylbis[(2-methoxyphenyl)phenylphosphane]), dppp (1,3-Bis(diphenylphosphino)propane), dppb (1,4-Bis(diphenylphosphino)butane), Chiraphos (2,3-Bis(diphenylphosphino)butane);
  phenyl-palladium-diphosphine chloride, bromide, or iodide, wherein the phosphine may be a phosphine according to formula (II) below;

a palladium-tetraphosphine, such as tetrakis(triphenylphosphine)-palladium (0), wherein the phosphine may be a phosphine according to formula (II) below;
tris-(dibenzylidene-acetone) palladium; and
allylpalladium (II) chloride dimer As described above, the homogenous palladium catalyst may comprise a phosphine according to formula (II)

$$P(R_{10}R_{11}R_{12}) \quad (II)$$

wherein
$R_{10}$, $R_{11}$, and, $R_{12}$, independently of each other, are selected from the group consisting of straight-chain or branched C1-C4 alkyl, aryl, such as phenyl, and heterorayl, such as furyl, wherein the aryl and the heteroaryl optionally are substituted by a straight-chain or branched a C1-C4 alkyl, a C1-C4 alkoxy, or a N(C1-4 alkyl)$_2$, wherein the alkyl groups may be the same or different.

Examples of inorganic and organic palladium salts to be complexed comprise chloride, bromide, iodide, nitrate, sulphate, acetate, and propionate salts of palladium. Further, also Na$_2$PdCl$_4$ may be used. Preferably the inorganic and organic palladium salts to be complexed are chloride, bromide, iodide, or acetate salts of palladium.

In some embodiments, a simple Pd-salt not being complexed is used. As long as the catalyst is dissolved in the solvent employed, any Pd-catalyst catalyzing coupling between the chloro-, bromo- or iodoisobenzofuran-1,3-dione and ethyne may be used. The use of complexed inorganic and organic palladium salts is however preferred.

Specific examples of homogenous palladium catalysts comprises (C$_6$H$_5$—CN)$_2$PdCl$_2$, (C$_6$H$_5$—CN)$_2$Pd(MeC(O)O$^-$)$_2$, (acetonitrile)$_2$PdCl$_2$, (acetonitrile)$_2$Pd(MeC(O)O$^-$)$_2$, (AsP[C$_6$H$_5$]$_3$)PdCl$_2$, (AsP[C$_6$H$_5$]$_3$)Pd(MeC(O)O$^-$)$_2$, (PPh$_3$)$_2$PdCl$_2$, (PPh$_3$)$_2$Pd(MeC(O)O$^-$)$_2$, C$_6$H$_5$PdI(PPh$_3$)$_2$, Pd(PPh$_3$)$_4$, Pd(P(tert-Bu)$_3$)$_4$, di-(dibenzylidene-acetone) palladium, di-(1,1-bis[dibenzylphosphine]-ferrocene)palladium dichloride, di-(1,1-bis[dibenzylphosphine]-ferrocene) palladium dibromide, di-(1,1-bis[dibenzylphosphine]-ferrocene)palladium diiodide.

According to an embodiment, the homogenous palladium catalyst is selected from the group consisting of palladium (II)dichloride, tetrakis(triphenylphosphine)-palladium (0), tris(dibenzylideneacetone)dipalladium(0), palladium(II)acetate, dichlorobis(triphenylphosphine)palladium(II), bis(acetonitrile) palladium(II), and bis(benzonitrile)palladium(II) dichloride.

According to an embodiment, the homogenous palladium catalyst is a complexed inorganic or organic palladium salt. The inorganic or organic palladium salt being complexed may be palladium chloride or palladium acetate. Further, the complexing agent may be a phosphine according to formula (II), such as triphenylphosphine.

It may be desirable and hence preferred to activate the homogenous palladium catalyst by adding one or more phosphines, such as a phosphine according to formula (II), or a chelating diphosphine, examples of which have been provided herein above, to the reaction mixture. An amount of the phosphine or the diphosphine of 100 to 2000 mol %, such as 200 to 500 mol %, relative to the palladium catalyst, may be used.

Phosphines may also be added as a phosphonium salt. As an example, compounds according to formula (II) may be added as a compound according to formula (IIb)

$$(R_{20}R_{21}R_{22})PH]BF_4 \quad (IIb)$$

wherein
$R_{20}$, $R_{21}$, and, $R_{22}$, independently of each other, are selected from the group consisting of straight-chain or branched C1-4 alkyl, aryl, such as phenyl and heterorayl, wherein the aryl and the heteroaryl optionally are substituted by a straight-chain or branched a C1-4 alkyl, a C1-4 alkoxy, or a —N(C1-4 alkyl)$_2$, wherein the alkyl groups may be the same or different.

As the homogenous palladium catalyst is acting catalytically, it is typically present in stoichiometric deficit with respect to the chloro-, bromo-, or iodoisobenzofuran-1,3-dione. According to an embodiment, the homogenous palladium catalyst is present in the reaction mixture in amount of 0.0005 to 5 mol %, such as 0.005 to 2 mol %, relative to the chloro-, bromo-, or iodoisobenzofuran-1,3-dione.

As already mentioned, the reaction between chloro-, bromo- or iodoisobenzofuran-1,3-dione and ethyne may be performed in the presence of a copper salt. Although Sonogashira couplings with arylhalides, such as arylbromides, typically are performed in the presence of copper, it is known that the need to include copper may be dispensed with, especially if an arylchloride is to be coupled. Thus, the reaction between chloro-, bromo- or iodoisobenzofuran-1,3-dione and ethyne, according to some embodiments are performed in the presence of copper, while it, according to some other embodiments are performed in the absence of copper.

According to an embodiment, wherein a bromobenzofuran-1,3-dione is to be reacted with ethyne, the reaction is performed in the presence of copper. According to another embodiment, wherein a chlororbenzofuran-1,3-dione is to be reacted with ethyne, the reaction is performed in the presence or in the absence of copper.

The copper salt may be copper (I) chloride, bromide, or iodide, or copper acetate. Preferably the copper salt is copper (I) iodide. While the active specie most likely is copper (I), copper (II) salts may, according to an embodiment, be used, as the copper (II) may be in situ reduced to copper (I). The copper salt, acting as a co-catalyst, may be present in the reaction mixture in an amount of 50 to 1000 mol %, such as 100 to 500 mol %, with respect to the homogenous palladium catalyst. According to an embodiment, the molar amount of copper is about equal to about twice the amount of palladium.

While the base may act as solvent as well, the reaction mixture typically comprises a solvent distinct from the base. Especially when scaling up the reaction, it may be advantageous to employ a solvent distinct from the base, as such solvents often are more economic. Further, the workup may be facilitated by employing a solvent distinct from the base.

A typically example of a solvent that may be employed is an aromatic hydrocarbon, such as toluene or xylene. Further, also polar aprotic solvents, such as dimethylformamide, dimethylacetamide, tetrahydrofuran and dimethylsulfoxide, may be used as solvent. By using a polar aprotic solvent, less washing agent, e.g. carboxylic acid, is needed in the washing step. In some embodiments, the washing step may even be dispensed with if a polar aprotic solvent is used. However, as polar aprotic solvents to some limited extent dissolve (ethyne-1,2-diyl)bis(isobenzofuran-1,3-dione), it may be preferred to employ an aromatic hydrocarbon as solvent in order to improve the yield.

Further examples of solvents that may be used comprise hydrocarbons, in particular aromatic hydrocarbons, such as benzene, toluene and xylene; ethers, such as tetrahydrofuran, dioxane, ethylene glycol dimethyl ether and diethylene glycol dimethyl ether; chlorinated hydrocarbons, such as chloroform and chlorobenzene; nitriles, such as acetonitrile, propionitrile and benzonitrile; amides, such as dimethyl formamide (DMF) and dimethylacetamide (DMAc), N-methylpyrrolidone (NMP), and hexamethylphosphoric acid triamide (HMPT); sulphoxides, such as dimethyl sulphoxide (DMSO).

According to an embodiment, the solvent is selected from the group consisting of aromatic hydrocarbons, nitriles, amides and sulphoxides. In such an embodiment, aromatic hydrocarbons are a preferred type of solvents.

As the anhydride moiety easily may be hydrolyzed, the solvent employed should preferably be anhydrous. Further, protic solvents, such as alcohols and primary and secondary amines, should be avoided as the may cause solvolysis, e.g. alcoholysis, of the anhydride moiety.

Various amount of the solvent may be used. According to an embodiment, the solvent and the amount of it, is selected in a manner such that the homogenous palladium catalyst is dissolved, while the formed (ethyne-1,2-diyl)bis(isobenzofuran-1,3-dione) precipitates, once formed. As an example, an amount of 80 to 2000 wt. %, preferably 100 to 1000 wt. %, relative to the amount of the chloro-, bromo-, or iodoisobenzofuran-1,3-dione, may be used. While it may be preferred to reduce the amount of solvent for various reasons, such as process economy, environmental stress, etc., it is preferred if the amount is sufficient to dissolve all of the homogenous palladium catalyst.

In addition to the homogenous palladium catalyst and optionally the copper salt, a base is also to be present in the reaction mixture. As already mentioned, the base should preferably be aprotic. Further, the base should preferably be non-nucleophilic.

According to an embodiment, the base is a trialkylamine, such as triethylamine. Further, also pyridine, or a derivative thereof, such as 4-dimethylaminopyridine, may be employed.

The base may also be a nitrogen base according to the formula (I)

$N(R_1R_2R_3)$    (I)

wherein
$R_1$ and $R_2$, independently of each another, are selected from straight-chain or branched C1-8 alkyl; or
$R_1$ and $R_2$ together are a C4-8 alkylene; wherein one carbon atom in the alkylene chain optionally is replaced by an oxygen atom or the group —$NR_4$—, wherein $R_4$ is a straight-chain or branched C1-4 alkyl; and
$R_3$ is a straight-chain or branched C1-4 alkyl.

Examples of bases according to formula (I) wherein $R_1$ and $R_2$, independently of each another, are selected from straight-chain or branched C1-C8 alkyl include triethylamine, tripropyl amine, tributyl amine, diisopropylethylamine.

Examples of bases according to formula (I) wherein $R_1$ and $R_2$ together are a C4-8 alkylene; wherein one carbon atom in the alkylene chain optionally is replaced by an oxygen atom or the group —$NR_4$—, wherein $R_4$ is a straight-chain or branched C1-C4 alkyl; include N-methylpyrrolidine, N-methylpiperidine, N-methylmorpholine, N-methylaza-cycloheptane, and N-methylaza-cyclooctane.

In an embodiment, wherein a solvent distinct from the base is present in the reaction mixture, the base is typically present in an amount corresponding to 80 to 600 mol %, such as 150 to 400 mol %, of the chloro-, bromo-, or iodoisobenzofuran-1,3-dione. In such an embodiment, the base is preferably present at least in an equimolar amount with respect to the chloro-, bromo-, or iodoisobenzofuran-1,3-dione.

In embodiment, wherein the base is employed as solvent as well, the amount of the base, may be selected in a manner such that the homogenous palladium catalyst is dissolved, while the formed (ethyne-1,2-diyl)bis(isobenzofuran-1,3-dione) precipitates. As an example, an amount of 80 to 2000 wt. %, preferably 100 to 1000 wt. %, relative to the amount of the chloro-, bromo-, or iodoisobenzofuran-1,3-dione, may be used.

Further, may the base be a aprotic bicyclic nitrogen compound such as, triethylenediamine (also known as diaza-bicyclo-octane or DABCO), 1,5-diazabicyclo[4.3.0]non-5-ene (also known as DBN) or 1,8-Diazabicyclo[5.4.0]undec-7-ene (also known as DBU)

Without further elaboration, it is believed that one skilled in the art may, using the preceding description, utilize the present invention to its fullest extent. The preceding preferred specific embodiments are, therefore, to be construed as merely illustrative and not limitative of the disclosure in any way whatsoever.

Although the present invention has been described above with reference to specific embodiments, it is not intended to be limited to the specific form set forth herein. Rather, the invention is limited only by the accompanying claims and, other embodiments than the specific above are equally possible within the scope of these appended claims, e.g. different than those described above.

In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous.

In addition, singular references do not exclude a plurality. The terms "a", "an", "first", "second" etc do not preclude a plurality.

EXAMPLES

The following examples are mere examples and should by no mean be interpreted to limit the scope of the invention. Rather, the invention is limited only by the accompanying claims.

All chemicals were purchased from different providers and used as received. Triethyl amine, toluene, dimethylformamide, dimethylacetamide, and acetic acid were purchased from VWR. Bis(triphenylphosphine)palladium(II) dichloride was purchased from Umicore. Triphenyl phosphine and copper iodide were purchased from Sigma-Aldrich. Acetylene was purchased from AGA.

Example 1

5,5'-(ethyne-1,2-diyl)bis(isobenzofuran-1,3-dione)

4-Bromophthalic anhydride (200 g), toluene (1 L) and triethyl amine (98 g) were mixed and purged with nitrogen. Thereafter, triphenylphosphine (2.08 g), bis(triphenylphosphine)palladium(II) dichloride (1.86 g) and copper iodide (1.00 g) were added. The resulting mixture was heated to 80° C. and subsequently purged with acetylene. Once the 4-bromophthalic anhydride had been consumed (as determined by HPLC subsequent to methanolysis), the mixture was filtered to obtain crude 5,5'-(ethyne-1,2-diyl)bis(isobenzofuran-1,3-dione). The obtained crude solid material was washed with 250 ml toluene twice. Thereafter, the resulting washed solid was re-slurried in 2 liters of glacial acetic acid and heated to 50° C., and stirred for 90 minutes. The mixture was then allowed to cool to 25° C., whereupon it was filtered. The resulting solid was washed with 2×100 ml acetic acid followed by 100 ml toluene. The wet product was dried under vacuum at 75° C., to yield 130 g (92%) 5,5'-(ethyne-1,2-diyl) bis(isobenzofuran-1,3-dione).

Example 2

5,5'-(ethyne-1,2-diyl)bis(isobenzofuran-1,3-dione)

5,5'-(ethyne-1,2-diyl)bis(isobenzofuran-1,3-dione) was obtained in a similar procedure as in example 1, except for the inclusion of an additional step wherein the acid washed product was reslurried in dimethylformamide before being dried under vacuum, providing 5,5'-(ethyne-1,2-diyl)bis(isobenzofuran-1,3-dione) in a yield of 80% and having a halogen content of less than 40 ppm by weight, as determined with ion chromatography Example 3

5,5'-(ethyne-1,2-diyl)bis(isobenzofuran-1,3-dione)

4-Bromophthalic anhydride (1200 g), toluene (4.8 L) and triethyl amine (642 g) were mixed and purged with nitrogen. Thereafter, triphenylphosphine (3.12 g), bis(triphenylphosphine)palladium(II) dichloride (2.78 g) and copper iodide (1.51 g) were added. The resulting mixture was heated to 73° C. and subsequently purged with acetylene, while controlling the reaction temperature at 80° C. Once the 4-bromophthalic anhydride had been consumed, which was determined by HPLC subsequent to methanolysis, acetic acid (3.6 L) was added and the resulting mixture was heated to 80° C. Mixture was filtered at 80° C., and resulting solid washed twice with 400 ml acetic acid. The resulting wet product was mixed with dimethylformamide (3.2 L) and heated at 130° C. during 2 hours, whereupon the mixture was cooled to 20° C. The mixture was filtered and washed twice with 400 ml dimethylformamide, followed by two washes of 400 ml ethyl acetate. The resulting product was dried at <100 mbar at 110° C., providing 5,5'-(ethyne-1,2-diyl)bis(isobenzofuran-1,3-dione) in a yield of 80% and high purity.

Example 4

5,5'-(ethyne-1,2-diyl)bis(isobenzofuran-1,3-dione)

4-Bromophthalic anhydride (22.5 kg), toluene (90 L) and triethyl amine (16.58 L) were mixed and purged with nitrogen. Thereafter, triphenylphosphine (58.49 g), bis(triphenylphosphine)palladium(II) dichloride (51.94 g) and copper iodide (28.38 g) were added. The resulting mixture was pressurized with acetylene (approximative 2 bar) and heated to 80° C. Once the 4-bromophthalic anhydride had been consumed, which was determined by HPLC subsequent to methanolysis, acetic acid (67.5 L) was added and the resulting mixture was heated to 80° C. Mixture was filtered at 80° C., and resulting solid washed twice with 7.4 L acetic acid. The resulting wet product was kept in a sealed plastic bag.

An additional batch was produced using the same procedure as mentioned above.

The average bromide content of the two batches was 1.4 wt %, calculated by comparing the NMR integrals of the triethylamine hydrobromide salt with the integrals of the product. As a significant amount of triethylammonium bromide, corresponding to a bromide content of more than 20 wt %, is formed in the reaction, it can be concluded that the wash with acetic acid is en effective way of reducing the bromide content.

The two batches of wet product were mixed with dimethylformamide (120 L) and heated at 130° C. during 2 hours, whereupon the mixture was cooled to 25° C. The mixture was filtered and washed twice with 15 L dimethylformamide, followed by two washes of 15 L ethyl acetate. The resulting product was dried at <100 mbar at 90° C., providing 20.7 kg 5,5'-(ethyne-1,2-diyl)bis(isobenzofuran-1,3-dione) in a yield of 66%. The bromide content of the final product was determined to be <30 ppm by ion chromatography. It was thus concluded that the bromide content may be reduced to trace amounts by applying an additional washing step.

Example 5

5,5'-(ethyne-1,2-diyl)bis(isobenzofuran-1,3-dione)

4-Bromophthalic anhydride (21.8 g), dimethylacetamide (66 ml) and triethyl amine (16 ml) were mixed and purged with nitrogen. Thereafter, triphenylphosphine (113 mg), bis(triphenylphosphine)palladium(II) dichloride (101 mg) and copper iodide (55 mg) were added. The resulting mixture was pressurized with acetylene (approximative 2 bar) and heated to 80° C. Once the 4-bromophthalic anhydride had been consumed, which was determined by HPLC subsequent to methanolysis, acetic acid (87 ml) was added and the resulting mixture was cooled to 40° C. Mixture was filtered, and resulting solid washed twice with 10 ml acetic acid. The resulting product was dried at <100 mbar at 110° C., providing 7.8 g 5,5'-(ethyne-1,2-diyl)bis(isobenzofuran-1,3-dione) in a yield of 51%. The bromide content of the final product was determined to be 150 ppm by ion chromatography.

Thus, 5,5'-(ethyne-1,2-diyl)bis(isobenzofuran-1,3-dione) with a low halogen content may be achieved by using a polar aprotic solvent, i.e. dimethylacetamide as solvent.

Example 6

5,5'-(ethyne-1,2-diyl)bis(isobenzofuran-1,3-dione)

5.8 g of the dry product from example 5 was mixed with dimethylformamide (23 ml) and heated at 130° C. during 2 hours, whereupon the mixture was cooled to 20° C. The mixture was filtered and washed twice with 3 ml dimethylformamide, followed by two washes of 3 ml ethyl acetate. The resulting product was dried at <100 mbar at 75° C., providing 4.8 g 5,5'-(ethyne-1,2-diyl)bis(isobenzofuran-1,3-dione) in an overall yield of 42%. The bromide content of the final product was determined to be less than 20 ppm by ion chromatography.

Example 7

Ion Chromatography

Approximately 1 g EBPA was weighed in to a glass-vial and subsequently 10.0 mL MilliQ $H_2O$ were added. The vial was sealed with a pressure-tight cap and heated to 105° C. for 24 h with continuous stirring. Blind (blank) samples were prepared identically. The resulting suspension was filtered using a 0.22 µm filter prior to analysis. Ion chromatography was performed on a Dionex ICS 900 system, comprised of a pump, a chemical suppressor cell and a conductivity detector. Separation was achieved using AG22 and AS22 anion-exchange guard- and analytical columns. The mobile phase was comprised of 4.5 mmol/l sodium carbonate and 1.4 mmol/l sodium bicarbonate and the flow rate was 1 ml/min. The ion chromatography system was calibrated using standard solutions of chloride and bromide in MilliQ $H_2O$.

CONCLUSIONS

As is apparent from example 1 to 6, 5,5'-(ethyne-1,2-diyl)bis(isobenzofuran-1,3-dione) may be obtained via the process described herein in high yields. Further, the purity of the obtained 5,5'-(ethyne-1,2-diyl)bis(isobenzofuran-1,3-dione) meets the requirements for incorporation of 5,5'-(ethyne-1,2-diyl)bis(isobenzofuran-1,3-dione) into poly- and oligoimides. Additionally, the process is deemed to be suitable also for large scale synthesis (cf. example 4).

The invention claimed is:

1. A process for obtaining (ethyne-1,2-diyl)bis(isobenzofuran-1,3-dione) comprising the steps of:
    reacting a chloro-, bromo-, or iodoisobenzofuran-1,3-dione with ethyne in an aprotic solvent, and in the presence of a dissolved, homogenous palladium catalyst, a base, and optionally a solvent distinct from the base, to obtain precipitated (ethyne-1,2-diyl)bis(isobenzofuran-1,3-dione); and
    separating the obtained precipitated (ethyne-1,2-diyl)bis(isobenzofuran-1,3-dione) from the reaction mixture.

2. The process according to claim 1, further comprising the step of washing the precipitated (ethyne-1,2-diyl)bis(isobenzofuran-1,3-dione) with a washing agent distinct from water and which dissolves the formed chloro, bromo or iodo salt of said base.

3. The process according to claim 2, wherein said wash is performed before, and/or after the separation of the obtained precipitated (ethyne-1,2-diyl)bis(isobenzofuran-1,3-dione) from the reaction mixture.

4. The process according to claim 2, wherein said step of washing the precipitated (ethyne-1,2-diyl)bis(isobenzofuran-1,3-dione) with a washing agent is performed at a temperature of 25 to 125° C.

5. The process according to claim 2, wherein said washing agent is selected from the group consisting of carboxylic acids, polar aprotic solvents, and chloroform.

6. The process according to claim 5, wherein said washing agent is formic acid or acetic acid.

7. The process according to claim 6, wherein said process further comprises the step of washing the acid washed, precipitated (ethyne-1,2-diyl)bis(isobenzofuran-1,3-dione) with a polar aprotic solvent.

8. The process according to claim 1, wherein said chloro-, bromo-, or iodoisobenzofuran-1,3-dione is a 5-haloisobenzofuran-1,3-dione and said (ethyne-1,2-diyl)bis(isobenzofuran-1,3-dione) is 5,5'-(ethyne-1,2-diyl)bis(isobenzofuran-1,3-dione).

9. The process according to claim 1, wherein said homogenous palladium catalyst is selected from the group consisting of bis(triphenylphosphine)palladium (II) dichloride, palladium (II) dichloride, tetrakis(triphenylphosphine)palladium (0), tris(dibenzylideneacetone)dipalladium (0), palladium (II) acetate, dichlorobis(triphenylphosphine)palladium (II), bis(acetonitrile) palladium (II), and bis(benzonitrile)palladium (II) dichloride.

10. The process according to claim 1, wherein the reaction between the chloro-, bromo- or iodoisobenzofuran-1,3-dione and ethyne, is performed in the presence of a copper salt.

11. The process according to claim 1, wherein the reaction mixture comprising said chloro-, bromo-, or iodoisobenzofuran-1,3-dione, said homogenous palladium catalyst, and said base, further comprises an aprotic solvent distinct from said base.

12. The process according to claim 1, wherein the step of reacting chloro-, bromo-, or iodoisobenzofuran-1,3-dione and ethyne is performed at a temperature of 60 to 100° C. and by applying an overpressure of ethyne over the reaction mixture comprising said chloro-, bromo-, or iodoisobenzofuran-1,3-dione, said homogenous palladium catalyst, and said base, and stirring the reaction mixture.

13. The process according to claim 1, wherein said base is an aprotic base.

14. The process according to claim 1, further comprising the step of drying the precipitated product under reduced pressure at elevated temperature.

15. The process according to claim 4, wherein said step of washing the precipitated (ethyne-1,2-diyl)bis(isobenzofuran-1,3-dione) with a washing agent is performed at a temperature of 40 to 75° C.

16. The process according to claim 5, wherein said carboxylic acid is selected from the group consisting of formic acid and acetic acid, and said polar aprotic solvent is selected from the group consisting of dimethylformamide, dimethylacetamide, dimethylsulfoxide, and N-Methyl-2-pyrrolidone.

17. The process according to claim 7, wherein said polar aprotic solvent is dimethylformamide, dimethylacetamide, dimethylsulfoxide, or N-Methyl-2-pyrrolidone.

18. The process according to claim 8, wherein said 5-haloisobenzofuran-1,3-dione is 5-bromoisobenzofuran-1,3-dione.

19. The process according to claim 10, wherein said copper salt is copper (I) chloride, bromide, or iodide, or copper (I) acetate.

20. The process according to claim 11, wherein said aprotic solvent being distinct from said base is selected from the group consisting of toluene and xylene, dimethylformamide, dimethylacetamide, tetrahydrofuran and dimethylsulfoxide.

21. The process according to claim 13, wherein said aprotic base is a nitrogen base according to the formula (I)

$N(R_1R_2R_3)$  (I)

wherein
$R_1$ and $R_2$, independently of each another, are selected from straight-chain or branched C1-8 alkyl; or
$R_1$ and $R_2$ together are a C4-8 alkylene; wherein one carbon atom in the alkylene chain optionally is replaced by an oxygen atom or the group $-NR_4-$, wherein $R_4$ is a straight-chain or branched C1-4 alkyl; and
$R_3$ is a straight-chain or branched C1-4 alkyl.

\* \* \* \* \*